US00PP27661P3

(12) United States Plant Patent
Wood

(10) Patent No.: US PP27,661 P3
(45) Date of Patent: Feb. 14, 2017

(54) ***WEIGELA* PLANT NAMED 'WFMOBLA'**

(50) Latin Name: *Weigela florida*
Varietal Denomination: WFMOBLA

(71) Applicant: Timothy Wood, Spring Lake, MI (US)

(72) Inventor: Timothy Wood, Spring Lake, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 14/756,872

(22) Filed: Oct. 21, 2015

(65) Prior Publication Data

US 2016/0128257 P1 May 5, 2016

Related U.S. Application Data

(60) Provisional application No. 62/122,541, filed on Oct. 22, 2014.

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Annette Para
(74) *Attorney, Agent, or Firm* — Cassandra Bright

(57) ABSTRACT

A new and distinct *Weigela* cultivar named 'WFMOBLA' is disclosed, characterized by a low, mounded plant habit requiring little pruning to maintain shape. Plants are very cold hardy and produce attractive glossy dark foliage. Dark foliage appears in the Spring when overwintered in a poly-house. The new. variety is a *Weigela*, normally produced as an outdoor garden or container plant.

2 Drawing Sheets

Latin name of the genus and species: *Weigela florida.*
Variety denomination: 'WFMOBLA'.

BACKGROUND OF THE INVENTION

The new *Weigela* cultivar is a product of a planned breeding program conducted by the inventor, Timothy D. Wood, in Grand Haven, Minn. The objective of the breeding program was to produce new *Weigela* varieties with low, mounded, dwarf plant habits, and improved production performance. The open pollination resulting in this new variety occured during May of 2009.

The seed parent is the commercial variety, *Weigela florida* 'Verweig' U.S. Plant Pat. No. 16,824. The pollen parent is unknown as it was an open pollination breeding program. The new variety was identified as a potentially interesting selection in June of 2011, at a greenhouse in Spring Lake, Minn.

Asexual reproduction of the new cultivar 'WFMOBLA' by softwood cuttings was first performed during June of 2011 at commercial greenhouse in Grand Haven, Minn. Subsequent propagation has shown that the unique features of this cultivar are stable and reproduced true to type in 4 successive generations.

SUMMARY OF THE INVENTION

The cultivar 'WFMOBLA' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'WFMOBLA' These characteristics in combination distinguish 'WFMOBLA' as a new and distinct *Weigela* cultivar:

1. Attractive, glossy dark burgundy black foliage.
2. Excellent hardiness.
3. Attractive low mounded habit that requires little care or pruning to maintain shape.
4. Dark foliage in the Spring when overwintered under poly-house greenhouse.

PARENT COMPARISON

Plants of the new cultivar 'WFMOBLA' are similar to plants of the seed parent, the commercial variety, *Weigela Florida* 'Verweig' U.S. Plant Pat. No. 16,824 in most horticultural characteristics, however, plants of the new cultivar 'WFMOBLA' differs in the following:

1. Dark burgundy black leaves, the parent has green, cream and pink variegated leaves.
2. Foliage has a higher gloss.
3. Clean Autumn foliage

COMMERCIAL COMPARISON

Plants of the new cultivar 'WFMOBLA' can also be compared to the commercial variety *Weigela* 'Elvera', U.S. Plant Pat. No. 12,217. These varieties are similar in most horticultural characteristics; however 'WFMOBLA' differs in the following:

1. Dark burgundy foliage under poly in Spring; Comparator foliage is a dirty green under the same conditions.
2. Hardier plant.
3. Stronger flowering.
4. Foliage is glossier.

BRIEF DESCRIPTION OF THE PHOTOGRAPHS

Figure 1:
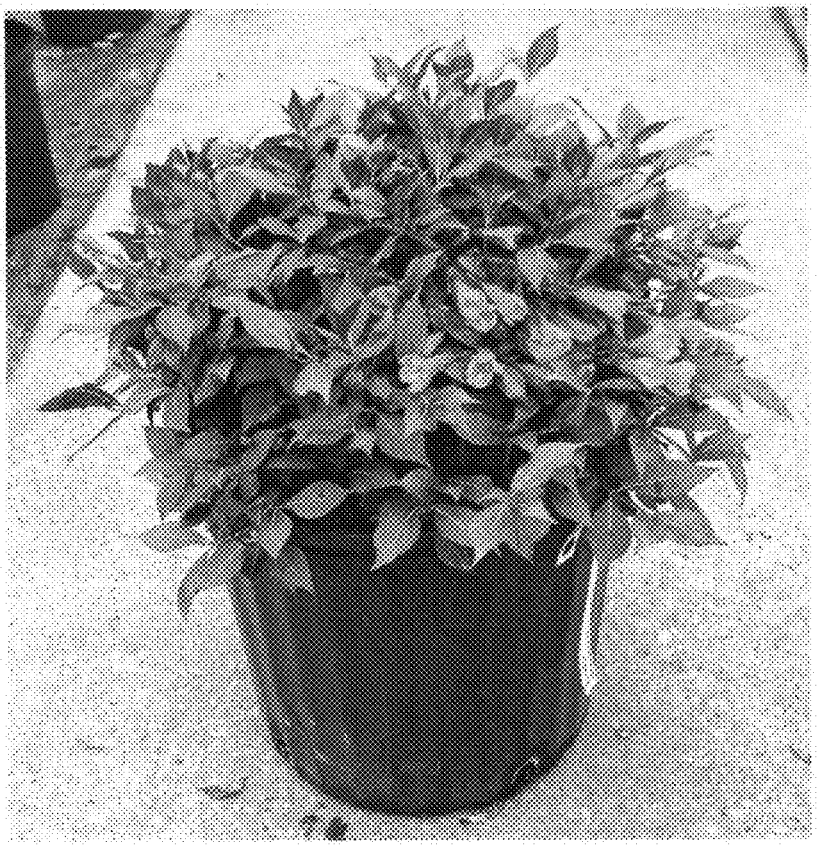

The accompanying photograph in FIG. 1 illustrates in full color a typical plant of 'WFMOBLA'.

Figure 2:
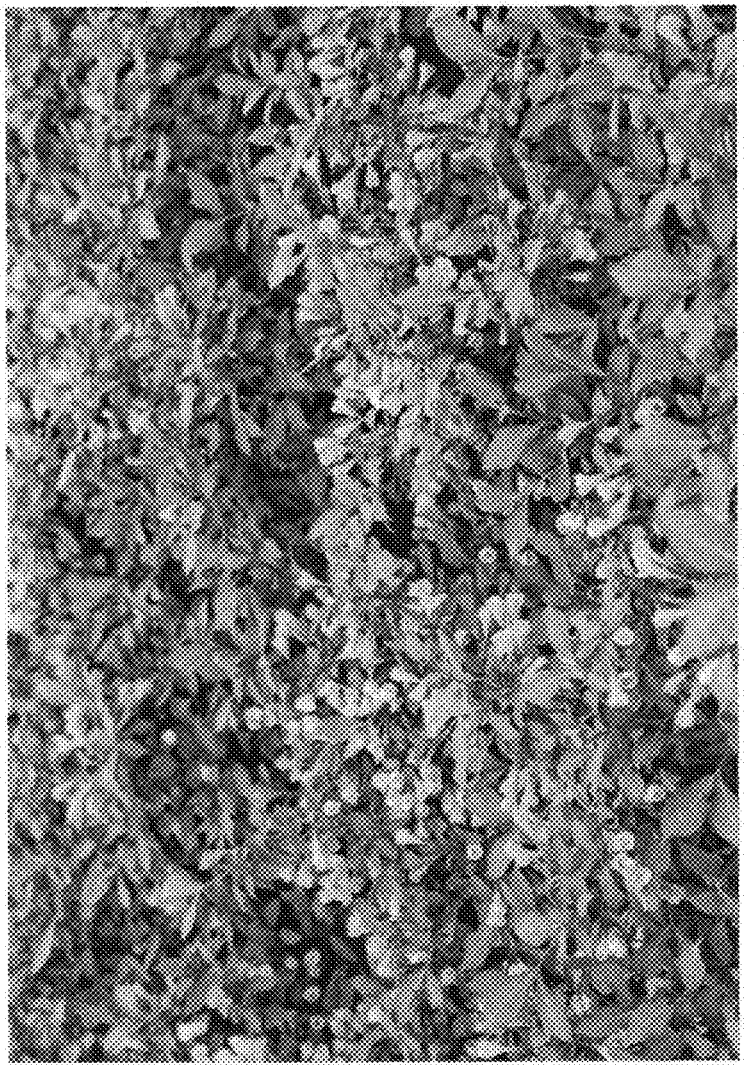

FIG. 2 illustrates in full color a typical foliage and flowers of 'WFMOBLA' grown in a greenhouse, in Grand Haven, Minn., in a commercial 1 gallon container. Age of the plant photographed is approximately 3 years. Plants were grown in a double poly covered greenhouse through the winter, and under shade cloth through the late spring and summer.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 1996 except where general terms of ordinary dictionary significance are used. The following observations and measurements describe 'WFMOBLA' plants grown in a commercial greenhouse in Grand Haven, Minn. Plants were grown in a double poly covered greenhouse through the winter, and under shade cloth through the late spring and summer. The description is of plants during Mid July of 2014. The plants were 3 years old and in 3 gallon containers. The growing temperature ranged from −31° C. to 38° C. Measurements and numerical values represent averages of typical plant types. Botanical classification: *Weigela florida* 'WFMOBLA'.

PROPAGATION

Time to initiate roots: About 15 days at approximately 27° C.

Root description: Fine, thin and freely branching.

Time to produce a rooted young plant: About 2 months at 27° C.

PLANT

Plant type: Shrub perennial.

Age of plant described: Approximately 3 years old.

Growth habit: Compact with good branching.

Pot size of plant described: 3 gallon pot.

Height: Approximately 27 cm to top of foliage.

Plant spread: Approximately 50 cm.

Growth rate: Medium.

Plant vigor: Strong.

Branching characteristics: Good, significant amount of basal and intermodal branching.

Length of primary lateral branches: Approximately 16.8 cm.

Diameter of lateral branches: Approximately 5 cm.

Quantity of lateral branches: About 12.

Stem:

- *Stem appearance*.—Rounded with ridges on opposite side 180° apart, on pubescent stem.
- *Stem color*.—Near RHS Brown 200B.
- *Pubescence*.—Yes, predominately on the ridges.
- *Aspect*.—Straight, occurring at an angle of approximately 40-45°.

Internode length: Average 2.5-3.5 cm.

FOLIAGE

Leaf:

- *Arrangement*.—Opposite.
- *Durability of foliage to stress*.—Very durable.
- *Quantity*.—Approximately 12 fully expanded per main branch.
- *Average length*.—Approximately 4.5 cm.
- *Average width*.—Approximately 2.5 cm.
- *Shape of blade*.—Ovate-oblanceolate.
- *Apex*.—Acuminate-Acute.
- *Base*.—Cuneate-attenuate.
- *Attachment*.—Stalked.
- *Margin*.—Serrulate.
- *Texture of top surface*.—Slightly pubescence, soft.
- *Texture of bottom surface*.—More pubescence than upper side, feels rougher and slightly gritty.
- *Color*.—Young foliage upper side: Near RHS Greyed-green 191A with Greyed-purple 187A around the edges. Young foliage under side: Near RHS Greyed-green 191A with Greyed-purple 187A around the edges. Mature foliage upper side: Near RHS Greyed-purple 187A. Mature foliage under side: Near RHS Greyed-purple 187A.
- *Venation*.—Type: Pinnate. Venation color upper side: Small veins Near RHS Greyed-purple 187B Aroungd the edges Greyed-green 197A; Midrib Yellow-green 145A. Venation color under side: Near RHS Greyed-purple 187B.
- *Petiole*.—Average Length: Approximately 5 mm. Diameter: Connection to leaf: 1 mm; Connecting to stem: 3 mm. Petiole color upper side:. Near RHS Yellow-green 145A. Petiole color lower side: Near RHS Yellow-green 145A. Petiole Texture upper side: Pubescent. Petiole Texture lower side: Pubescent.
- *Other foliage characteristics*.—Dimensional, subtle fade between purple and red groups on foliage.

FLOWER:

Natural flowering: Early to late Spring.

Flower arrangement: Single salverform flowers, mostly terminal.

Inflorescence type and habit: Umbel.

Quantity of flowers per inflorescence: About 4-6.

Inflorescence size: Width: Approximately 4 cm. Height: Approximately 6.5 cm.

Individual flowers:

- *Flower form*.—Salverform.
- *Flower aspect*.—Upright and slightly outward.
- *Size*.—Diameter: Approximately 1 cm. Length: Approximately 3.3 mm. Tube length: 1.5 cm. Tube base diameter: 3 mm. Flower throat diameter, top: 3 mm.
- *Flower other characteristics*.—Flower tube color: Lightly shaded near RHS Red-purple 70B. Flower throat color: Near RHS yellow-orange 22A with slight striation of RHS White 155A. Persistence: Self cleaning. Fragrance: None.

Petal:

- *Petal arrangement*.—Whorl petals fused at opening of throat.
- *Number of petals per flower*.—4.
- *Petal appearance*.—Smooth, slight color variation.
- *Petal shape*.—Rounded-orbicular.
- *Margin*.—Entire, slightly undulate.
- *Tip shape*.—Obtuse.
- *Length*.—1.2 cm.

*Width*.—9 mm.
*Texture*.—Upper: Smooth, soft, delicate. Lower: Smooth, soft, delicate. Throat; Soft, smooth.

Petal color:
*When opening*.—Upper surface: Near RHS Red-purple 66D at tip fading into red-purple 64A at base. Lower surface: Soft fade near RHS Red-purple 66A.
*Fully opened*.—Upper surface: Near RHS Red-purple 66D at tip fading into red-purple 64A at base. Lower surface: Near RHS Red-purple 66A.
*Petal vein color*.—Upper side: Near RHS Purple 75B. Lower Side: Near RHS Red-purple 6A well blended.

Bud:
*Shape*.—Obovate.
*Length*.—Approximately 3.4 cm.
*Diameter*.—Approximately 1 cm.
*Color*.—Near RHS Red-purple 59A.

Sepals:
*Shape*.—Narrowly triangular.
*Arrangement*.—Unguiculate, fused at base.
*Number of sepal*.—5.
*Length*.—Approximately 1 cm.
*Width*.—Approximately 3 mm.
*Calyx shape*.—Uniguiculate.
*Margin*.—Entire.
*Base*.—Obtuse.
*Tip*.—Acuminate.
*Texture*.—Smooth, conaceous.
*Color*.—Upper side: Near RHS Red-purple 59A lightly shaded. Lower side: Near RHS Red-purple 59B.

Pedicel:
*Length*.—Average 1.5 cm.
*Diameter*.—2 mm.
*Color*.—Near RHS Red-Purple 59A with slight striation of Yellow-green 145A.
*Strength*.—Good.
*Texture*.—Smooth, coriaceous, slightly pubescent.

Peuncle: No true peduncle, inflorescence arises from branch.

REPRODUCTIVE ORGANS

Stamens:
*Number*.—5.
*Filament length*.—Approximately 1.6 cm.
*Filament color*.—Near RHS White 155A blended with Red-purple 58A.

Anthers:
*Shape*.—Linear, slightly oblong.
*Length*.—Approximately 8 mm.
*Color*.—Near RHS Greyed-yellow 161D.
*Pollen*.—Not observed.

Pistil:
*Number*.—1.
*Length*.—Approximately 2.5 cm.
*Style*.—Length: Approximately 3 cm. Color: Near RHS white 155A blended with Red-purple 58A.
*Stigma*.—Shape: Globular, flat-bottomed, lobed. Color: Near RHS Greyed-yellow 160D. Ovary color: Near RHS Red-purple 59A.

OTHER CHARACTERISTICS

Seeds and fruits: Not observed to date.
Garden performance: Excellent.
Disease/pest resistance: Good mildew resistance.
Temperature tolerance: The new variety tolerates temperatures between −31 to 38° C.

What is claimed is:

1. A new and distinct cultivar of *Weigela* plant named 'WFMOBLA' as herein illustrated and described.

* * * * *